United States Patent
Yamamoto et al.

(10) Patent No.: US 8,652,419 B2
(45) Date of Patent: Feb. 18, 2014

(54) METHOD OF MANUFACTURING MICROFLUIDIC CHIP, MICROFLUIDIC CHIP, AND APPARATUS FOR GENERATING SURFACE PLASMON RESONANT LIGHT

(71) Applicant: Fujikura Ltd., Tokyo (JP)

(72) Inventors: Satoshi Yamamoto, Sakura (JP); Tatsuo Suemasu, Sakura (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 13/758,450

(22) Filed: Feb. 4, 2013

(65) Prior Publication Data
US 2013/0140976 A1 Jun. 6, 2013

Related U.S. Application Data

(63) Continuation of application No. PCT/JP2011/067204, filed on Jul. 28, 2011.

(30) Foreign Application Priority Data

Aug. 6, 2010 (JP) ................. 2010-177948

(51) Int. Cl.
*B05D 3/06* (2006.01)
*B05D 3/10* (2006.01)
(52) U.S. Cl.
USPC .......................................... 422/505; 422/502
(58) Field of Classification Search
USPC ........ 313/325–326; 216/37–39; 422/502, 505
See application file for complete search history.

(56) References Cited

FOREIGN PATENT DOCUMENTS

| JP | 2005-353576 A | 12/2005 |
|---|---|---|
| JP | 2006-208069 A | 8/2006 |
| JP | 2008-286778 A | 11/2008 |
| JP | 2010-050138 A | 3/2010 |

OTHER PUBLICATIONS

International Search Report issued in Application No. PCT/JP2011/067204 dated Nov. 1, 2011.
Keiko Tawa et al. Optical microscopic observation of fluorescene enhanced by grating-coupled surface plasmon resonance, Optics Express, 2008, vol. 16, No. 13, 9781-9790.
Naohiro Furukawa et al., Formation of subwavelength optical elements inside a microfluidic channel using femtosecond laser lithography, 16th Symposium on Microjoining and Assembly Technology in Electronics, Feb. 2-3, 2010, Yokohama.

(Continued)

*Primary Examiner* — Anh Mai
*Assistant Examiner* — Elmito Breval
(74) *Attorney, Agent, or Firm* — Sughrue Mion, PLLC (57) ABSTRACT

A method of manufacturing a microfluidic chip includes: irradiating, with a laser light, an area to be provided with a valley for storing a fluid on a surface of a substrate so as to form a modified region having a periodic pattern formed in a self-organizing manner in a light-collecting area of the laser light, the laser light having a pulse width for which the pulse duration is on the order of picoseconds or less; carrying out an etching treatment on the substrate in which the modified region is formed, removing at least some of the modified portion so as to provide the valley, and forming a periodic structure having a plurality of groove portions along one direction which have a surface profile based on the periodic pattern on at least a bottom surface of the valley; and forming a metal layer that covers the periodic structure of the bottom surface.

11 Claims, 7 Drawing Sheets

(56) References Cited

OTHER PUBLICATIONS

Simova E., et al., Femtosecond laser-induced long-range self-organized periodic planar nanocracks for applications in biophotonics, Proceedings of SPIE, May 17, 2007 (received date), vol. 6458, pp. 64581B.1-64581B.14.

Yasuhiko Shimoma, Chotan Pulse Laser ni yoru Nano Kozo no Keisei to sono Oyo, Optronics, Feb. 10, 2007, vol. 26, No. 2, pp. 114-117.

METHOD OF MANUFACTURING MICROFLUIDIC CHIP, MICROFLUIDIC CHIP, AND APPARATUS FOR GENERATING SURFACE PLASMON RESONANT LIGHT

CROSS REFERENCE TO RELATED APPLICATIONS

This application is a continuation application based on a PCT Patent Application No. PCT/JP2011/067204, filed Jul. 28, 2011, whose priority is claimed on Japanese Patent Application No. 2010-177948, filed Aug. 6, 2010, the entire content of which are hereby incorporated by reference.

BACKGROUND OF THE INVENTION

1. Field of the Invention

The present invention relates to a method of manufacturing a microfluidic chip, a microfluidic chip, and an apparatus for generating surface plasmon resonant light.

2. Description of the Related Art

In the past, a molecular interaction detecting apparatus using surface plasmon resonance which is induced by radiating light a metal surface with light was known.

For example, Japanese Unexamined Patent Application, First Publication No. 2006-208069 discloses an apparatus in which a metal thin film is formed at a detecting portion of a flow channel which allows a solution including biological molecules to flow through, an antibody modified by a fluorescent molecule is fixed to the surface of the metal thin film, and changes in fluorescent signals from the fluorescent molecule can be detected when molecular interaction (bonding) occurs between the antibody and a detection subject.

In the apparatus described in Japanese Unexamined Patent Application, First Publication No. 2006-208069, generally, a prism is required in order to irradiate, with a laser light, the surface of the metal thin film at a specific incident angle.

There was a problem in that the size of the apparatus inevitably increases for the control of the laser radiation angle and the like.

In contrast to this, in the micro blade described in Japanese Unexamined Patent Application, First Publication No. 2008-286778 and a surface plasmon excitation-enhanced fluorescent microscope using the micro blade, the limitation in the laser radiation angle can be alleviated by forming a regular periodic structure (grating) on the metal surface of a detecting portion.

Therefore, it is disclosed that a decrease in the size of the apparatus and the simplification of an optical system can be achieved with no need for the prism.

A usual conventional method of forming the periodic structure is a method in which a resist mask having a periodic pattern that corresponds to the periodic structure is formed on a substrate made of SiO2 or the like, and the substrate is etched.

For example, there is a method in which a grating-like resist mask is formed by radiating, with a He—Cd laser, a positive-type resist using a double-beam interference method ("Optical microscopic observation of fluorescence enhanced by grating-coupled surface plasmon resonance" Keio Tawa, et al. OPTICS EXPRESS, 2008, Vol. 16, No. 13, 9781-9790).

In addition, a method in which a negative-type resist is coated on a flow channel formed on a SiO2 substrate, and the resist is worked into a grating using dual-photon absorptiometry in which a femtosecond laser is used ("Formation of subwavelength optical elements inside a microfluidic channel using femtosecond laser lithography" Norihiro Furukawa, Hiroaki Nishiyama, Yoshinori Hiratal 6th Symposium on "Microjoining and Assembly Technology in Electronics", Feb. 2-3, 2010, Yokohama).

However, in any of the above methods, it is necessary to form a resist which has a shape corresponding to the periodic structure and has been subjected to an ultrafine working on the substrate.

That is, there is a problem in that the working accuracy of the periodic structure is dependent on the working accuracy of the resist.

The working accuracy of the resist is influenced by complicated factors such as the chemical composition of a resist composition, the adhesiveness between the substrate and the resist, etching characteristics after formation of the resist pattern, laser irradiation conditions, and the like.

In addition, there are frequent cases in which it is difficult to uniformly form a non-patterned resist in the fine structures of the microfluidic channel and the like on the substrate.

The invention has been made in consideration of the above circumstances, and an object of the invention is to provide a method of manufacturing a microfluidic chip in which a periodic pattern and a periodic structure can be directly formed on the surface of a substrate with no need of forming a resist having the periodic pattern that corresponds to the periodic structure; the microfluidic chip, and a surface plasmon resonance analyzing apparatus.

SUMMARY (1) A method of manufacturing a microfluidic chip according to a first aspect of the invention includes radiating, with a laser light having a pulse width for which the pulse duration is on the order of picoseconds or less, an area provided with a valley for storing a fluid on the surface of a substrate so as to form a modified region having a periodic pattern formed in a self-organizing manner in a light-collecting area of the laser light (Process A); carrying out an etching treatment on the substrate in which the modified region is formed, removing at least some of the modified portion so as to provide the valley, and forming a periodic structure including a plurality of groove portions along one direction which have a surface profile based on the periodic pattern on at least the bottom surface of the valley (Process B); and forming a metal layer that covers the periodic structure of the bottom surface (Process C).

(2) In the method of manufacturing a microfluidic chip according to the above (1), the periodic pattern formed in a self-organizing manner may include portions modified by the constructive interference of interference waves of a plasmon in an area near the surface of the substrate which is generated by the laser light incident to the substrate and the incident laser light, and portions modified by the destructive interference of the interference waves.

(3) The method of manufacturing a microfluidic chip according to the above (1) or (2) may employ a configuration including using a linear polarized laser as the laser light, and scanning the light-collecting area of the laser light in the vertical direction to the polarized wave direction of the linear polarized light so that the scanning direction and a direction in which the plurality of groove portions which form the periodic structure is stretched are parallelized.

(4) The method of manufacturing a microfluidic chip according to the above (1) or (2) may employ a configuration including using a linear polarized laser as the laser light, and scanning the light-collecting area of the laser light in the parallel direction to the polarized wave direction of the straight polarized light so that a direction in which the plurality of groove portions which form the periodic structure is stretched are made to be vertical to the scanning direction.

(5) In the method of manufacturing a microfluidic chip according to any one of the above (1) to (4), an isotropic dry etching method may be used in the etching treatment.

(6) In the method of manufacturing a microfluidic chip according to any one of the above (1) to (5), the valley provided on the surface of the substrate may form a flow channel.

(7) The method of manufacturing a microfluidic chip according to the above (6) may further include attaching a member to the surface of the substrate so as to cover the flow channel on the surface of the substrate.

(8) In the method of manufacturing a microfluidic chip according to any one of the above (1) to (5), the valley provided on the surface of the substrate may form a well.

(9) The method of manufacturing a microfluidic chip according to any one of the above (1) to (8) may further include forming a protective layer on the metal layer.

(10) A microfluidic chip according to a second aspect of the invention is a microfluidic chip obtained using the manufacturing method according to any one of the above (1) to (9).

(11) An apparatus for generating surface plasmon resonant light according to a third aspect of the invention is an apparatus for generating surface plasmon resonant light in which the microfluidic chip according to the above (10) is used.

According to the method of manufacturing a microfluidic chip according to the first aspect of the invention, since it is possible to form the valley and the periodic structure using the same process, the manufacturing efficiency is excellent.

In addition, since the periodic structure is formed in the valley using modification of the substrate through laser radiation and the etching treatment, the working accuracy of the periodic structure is excellent.

It is also possible to form a periodic structure on the order of nanometers.

In addition, according to the method of manufacturing a microfluidic chip according to the first aspect of the invention, it is possible to dispose a flow channel having a desired path and shape and/or a well having a desired shape on a substrate.

Furthermore, a periodic structure on the order of nanometers (grating) can be formed on the desired bottom surface portions in the flow channel or well.

Furthermore, a metal layer having a surface profile that reflects the periodic structure can be formed by covering the periodic structure with the metal layer.

It is possible to induce surface plasmon resonant light in the vicinity of the metal layer by radiating, with light from the outside, the metal layer.

Use of the surface plasmon resonant light enables applications such as detection of molecular interactions in the vicinity of the metal layer or observation of an observation subject present in the vicinity of the metal layer using fluorescent signals.

DETAILED DESCRIPTION OF THE PREFERRED EMBODIMENTS

Hereinafter, preferable embodiments of the invention will be described with reference to the accompanying drawings.

<Method of Manufacturing a Microfluidic Chip>

A method of manufacturing a microfluidic chip according to a first embodiment of the invention includes a process A in which, an area provided with a valley for storing a fluid on the surface of a substrate is irradiated with a laser light having a pulse width for which the pulse duration is on the order of picoseconds or less, so as to form a modified region having a periodic pattern formed in a self-organizing manner in a light-collecting area of the laser light, a process B in which an etching treatment is carried out on the substrate in which the modified region is formed, at least some of the modified portion is removed so as to provide the valley, and a periodic structure including a plurality of groove portions along one direction which have a surface profile based on the periodic pattern is formed on at least the bottom surface of the valley, and a process C in which a metal layer that covers the periodic structure of the bottom surface is formed.

[Process A]

Figure 1:
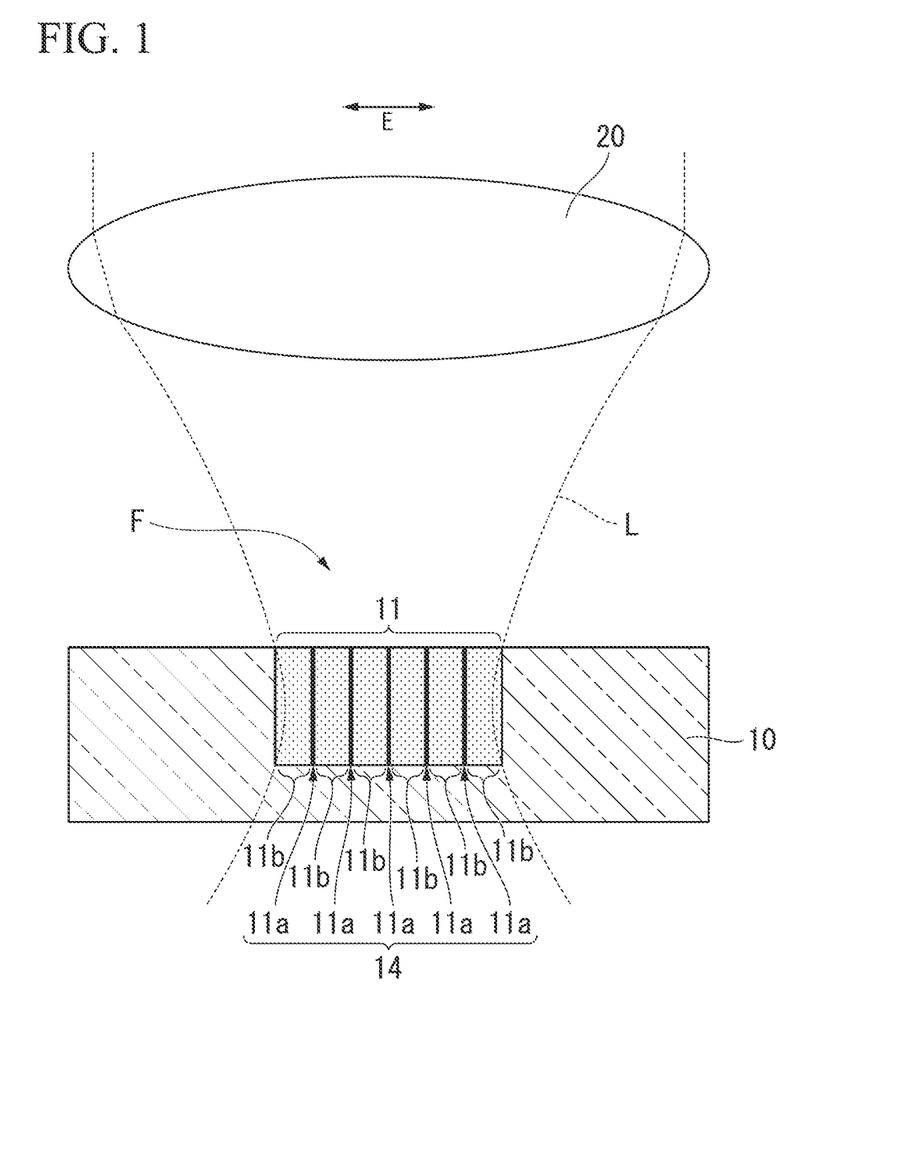
FIG. 1 is a schematic cross-sectional view of a substrate showing an appearance in which a modified region including a periodic pattern is formed on the surface of a substrate through laser radiation.

As shown in FIG. 1, the process A is a process in which an area provided with a valley for storing a fluid on the surface of a substrate is irradiated with a laser light having a pulse width for which the pulse duration is on the order of picoseconds or less so as to form a modified region having a periodic pattern formed in a self-organizing manner in a light-collecting area of the laser light.

In the schematic cross-sectional view of FIG. 1, a substrate 10 is irradiated with a laser light L.

The laser light L is collected in an area near the surface of the substrate using a lens 20.

A modified region 11 is formed in a light-collecting area F of the laser light L in the substrate 10.

The focal point of the laser light L is present in the light-collecting area F.

In addition, in FIG. 1, linear polarized laser is used as the laser light L, and the polarized wave direction (electric field direction) is a direction parallel to the paper surface (indicated by the two headed arrow E).

The modified region 11 includes a plurality of first modified regions 11a and a plurality of second modified regions 11b.

When seen in the polarized wave direction which is a direction parallel to the paper surface, a periodic pattern 14 in which the first modified regions 11a and the second modified regions 11b are alternately formed is present in the modified region 11.

The first modified regions 11a are portions that are modified as a result of the constructive interference of interference waves of a plasmon (electronic plasma wave) in an area near the surface of the substrate which is generated by the laser light L incident to the substrate 10 and the incident laser light L.

In contrast, the second modified regions 11b are formed at portions in which the constructive interference of the interference waves is relatively weak.

Since the modified region 11 has a weakened etching resistance (the etching rate is fast), the modified region is preferentially removed in the etching treatment in the process B described below.

Furthermore, since the first modified regions 11a and the second modified regions 11b have different structures, the etching rate becomes faster in one of the regions than the other (herein, the etching rate is considered to be faster in the first modified regions 11a for convenience).

The periodic pattern 14 is influenced by the interference waves and formed in a self-organizing manner.

That is, it is possible to form the modified region 11 in accordance with the periodic pattern 14 directly on the substrate 10 without using a resist mask or the like by controlling the irradiation intensity of the laser light L so that the interference waves are generated.

In other words, in the method of manufacturing a microfluidic chip according to the embodiment, the periodic pattern 14 formed in a self-organizing manner preferably includes a plasmon in an area near the surface of the substrate which is generated by the laser light L incident to the substrate 10, portions modified by the constructive interference of interference waves with the incident laser light L (the first modified regions 11a), and portions modified by the destructive interference of the interference waves (the second modified regions 11b).

The irradiation intensity is preferably a value close to the optimal working value of a material that configures the substrate 10, or the optimal working value or more and the ablation threshold or less.

The periodic pattern 14 can be formed in a self-organizing manner in an area near the light-collecting area of the laser light L by achieving the above irradiation intensity.

Here, the optimal working value is defined as the lower limit value of a laser pulse power for forming the periodic structure 14.

In addition, the ablation threshold refers to the lower limit value of a laser pulse power for generating ablation, and is different from the optimal working value.

In general, a smaller value than the ablation threshold is used as the optimal working value.

The periodic pattern 14 on the order of nanometers can be formed by appropriately adjusting the irradiation intensity.

Here, the order of nanometers refers to a fact that the gap between the adjacent modified regions 11a or the gap between the adjacent modified regions 11b is of the unit of nanometers (nm).

For example, the periodic pattern 14 having the above gap of 10 nm to 800 nm can be formed.

The material that configures the substrate 10 is preferably a material which allows the periodic pattern 14 to be formed in a self-organizing manner on the surface of the substrate 10 through the process A, and has a high transmittance with respect to the laser light L.

For example, the material is most preferably silica glass which is excellent in terms of workability, and, additionally, preferable examples thereof also include other glass materials such as borosilicate glass and crystalline materials such as quartz, sapphire, and diamond.

The laser light L is not particularly limited as long as the pulse duration has a pulse width on the order of picoseconds or less, and examples of the laser light that can be used include titanium sapphire laser, fiber laser having a pulse width on the order of picoseconds or less, and the like.

As the lens 20 that collects the laser light L, for example, a refractive object lens or a refractive lens can be used.

In addition, Fresnel, reflective, oil immersion-type, and water immersion-type object lenses may be used.

When a cylindrical lens is used, it becomes possible to irradiate with the laser, a wide range of the surface of the substrate 10 in a single process.

In addition, it is also possible to work a wide range of area in a single process using a holographic mask, interference, or the like.

The irradiation method of the laser light L is not particularly limited.

For example, when the laser light L is radiated while being moved in a direction parallel to the surface of the substrate 10, the scanning range of the light-collecting area of the laser light L becomes wide, and the modified region 11 having the periodic pattern 14 in a wide range can be formed.

In addition, for example, when the laser light L is radiated so that irradiated portions overlap in a direction parallel to the laser propagation direction (the substrate thickness direction), the periodic pattern 14 can be formed in the substrate thickness direction without deviation.

Examples of radiation of the laser light L include a case in which a Ti sapphire laser is used.

Regarding the irradiation conditions, the laser light L is collected and radiated to a synthetic silica substrate 10 under the set irradiation conditions of, for example, a wavelength of 800 nm, a repetition frequency of 200 kHz, and a laser scanning rate of 1 mm/second.

In contrast, the values of the wavelength, repetition frequency, and scanning rate exemplified herein are an example, and the invention is not limited thereto, and can be arbitrarily varied.

As the lens 20 used for light collection, an object lens having N.A<0.7 is preferably used.

Regarding the pulse intensity (laser radiation intensity), when an area near the surface of the substrate is irradiated with the laser, a power of the laser is preferably the ablation threshold or less, for example, a power of approximately 100 nJ/pulse or less.

The modified region 11 can be formed into a desired shape in the substrate 10 by scanning the light-collecting area of the laser light while pointing the focal point of the laser light L onto the substrate 10.

After that, at least some of the modified region 11 is removed through the etching treatment in the subsequent process B so that a valley is provided on the surface of the substrate.

That is, it is possible to form a valley on the surface of the substrate 10 by irradiating, with the laser light L, an area provided with the valley for storing a fluid (specimen solution) on the surface of the substrate 10 so as to form the modified region 11 in the above area, and removing some of the modified region 11 through an etching treatment.

At this time, a periodic structure including a plurality of groove portions along one direction which have a surface profile based on the periodic pattern 14 can be formed on the bottom surface of the valley.

It is possible to adjust the relationship between the direction of the periodic pattern 14 formed in the modified region 11 (the direction in which the first modified regions 11a and the second modified regions 11b alternately appear) and the stretching direction of the modified region 11 along the scanning direction of the light-collecting area of the laser light L by controlling the polarized wave direction (polarization) of the laser light L.

Figure 2:
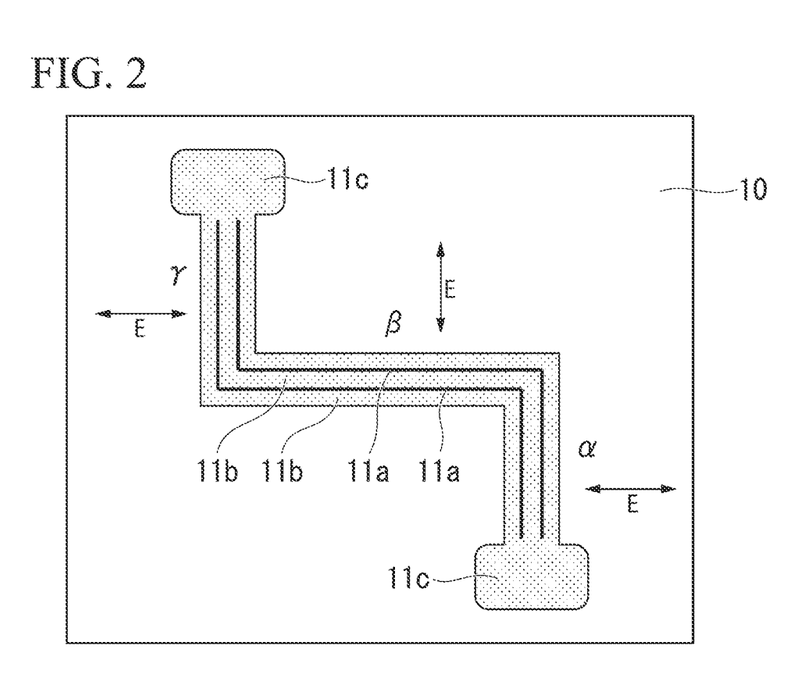
FIG. 2 is an example of a schematic top view of the substrate showing the relationship between the scanning direction (stretching direction of the modified region) of irradiation laser light and the direction of the periodic pattern.

FIG. 2 shows an example of the relationship between the stretching direction of the modified region 11 and the polarized wave direction of the laser light L.

FIG. 2 is a schematic top view of the substrate 10.

The modified region 11 is formed by using a linear polarized laser as the laser light L, irradiating the linear polarized laser onto the substrate 10 from the vertical direction to the surface of the substrate (paper surface), and continuously scanning the light-collecting area along the stretching direction of the modified region 11 in the order of α, β, and γ.

The polarized wave direction E (electric field direction) of the laser light L at this time is indicated by the two headed arrow E.

In the example of FIG. 2, in the respective areas of α to γ, the laser light L is scanned while the polarized wave direction E is controlled so that the scanning direction of the laser light L (the stretching direction of the modified region 11) and the polarized wave direction E become vertical to each other.

As a result, the first modified regions 11a and the second modified regions 11b are formed in parallel along the stretching direction of the modified region 11.

In addition, as is evident from the drawing, the periodic pattern 14 is formed in a direction that intersects the stretching direction of the modified region 11.

In contrast, in the example of FIG. 2, the first modified regions 11a are drawn using two heavy lines. However, the first modified regions are drawn using two lines only for convenience in consideration of the circumstance of the paper surface, and it is not meant that the first modified regions 11a are two lines in the modified region 11 in practice.

Figure 3:
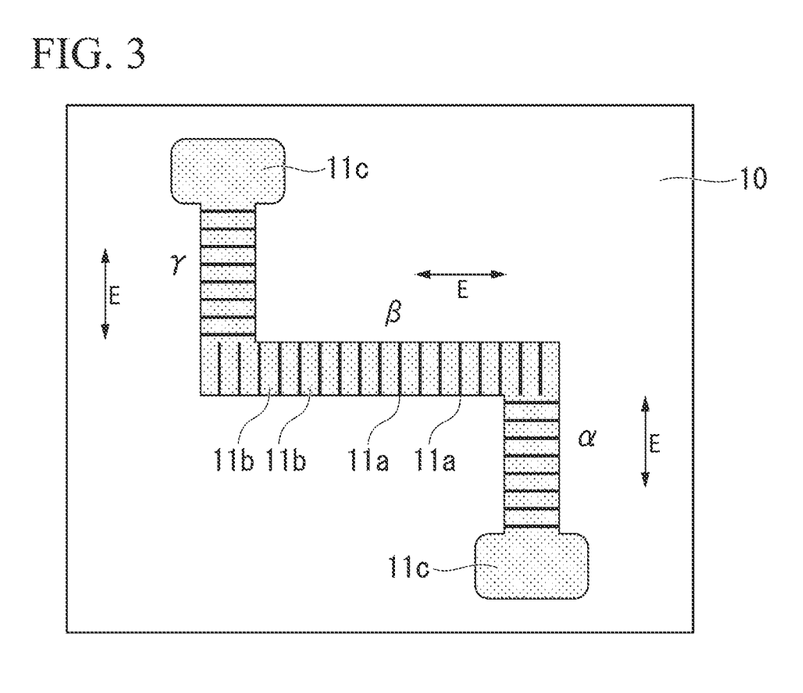
FIG. 3 is another example of the schematic top view of the substrate showing the relationship between the scanning direction (stretching direction of the modified region) of irradiation laser light and the direction of the periodic pattern.

FIG. 3 shows another example of the relationship between the stretching direction of the modified region 11 and the polarized wave direction of the laser light L.

FIG. 3 is a schematic top view of the substrate 10.

The modified region 11 is formed by using a linear polarized laser as the laser light L, irradiating, with the linear polarized laser, the substrate 10 from the vertical direction to the surface of the substrate (paper surface), and continuously scanning the light-collecting area along the stretching direction of the modified region 11 in the order of α, β, and γ.

The polarized wave direction E (electric field direction) of the laser light L at this time is indicated by the two headed arrow E.

In the example of FIG. 3, in the areas of α to γ, the laser light L is scanned while the polarized wave direction E is controlled so that the scanning direction of the laser light L (the stretching direction of the modified region 11) and the polarized wave direction E become vertical to each other.

As a result, the first modified regions 11a and the second modified regions 11b are formed so as to intersect the stretching direction of the modified region 11.

In addition, as is evident from the drawing, the periodic pattern 14 is formed in a direction parallel to the stretching direction of the modified region 11.

In the examples of FIGS. 2 and 3, the periodic pattern 14 is not formed in third modified regions 11c at both ends of the modified region 11.

This is because the irradiation intensity of the laser light L is controlled so that the third modified regions 11c are formed using a stronger pulse power than when the periodic pattern is formed in a self-organizing manner.

As such, it is possible to determine whether to form the periodic pattern 14 or not by controlling the laser radiation intensity.

For example, it is also possible not to form the periodic pattern 14 in at least some of the areas α to γ.

In addition, in the examples of FIGS. 2 and 3, the modified region 11 is formed in a crank shape.

In this case, after the etching treatment ends in the process B, the crank-shaped modified region 11 is removed from the surface of the substrate 10, and a crank-shaped valley is formed.

The shape of the modified region 11 is not limited to the crank shape, and it is possible to form the modified region in a desired shape by controlling the scanning of the laser light L in accordance with the shape of the flow channel or well in the microfluidic chip according to the invention.

[Process B]

Figure 4:
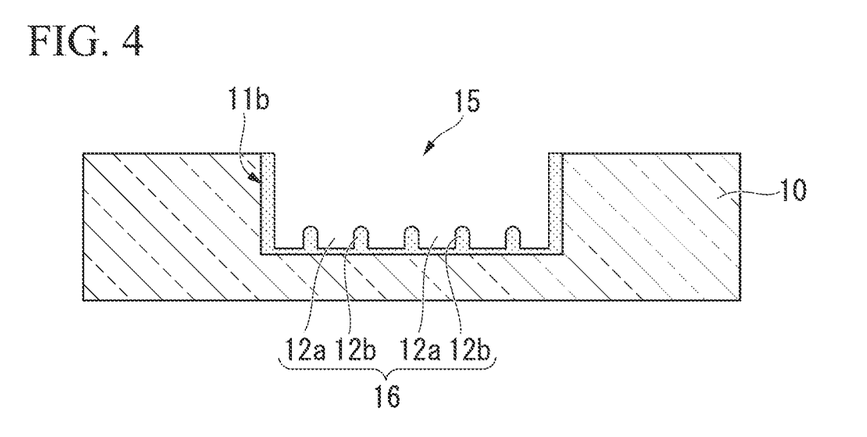
FIG. 4 is a schematic cross-sectional view of the substrate showing an appearance in which a valley is formed on the surface of the substrate, and a periodic structure is formed on the bottom surface of the valley.

As shown in FIG. 4, the process B is a process in which an etching treatment is carried out on the substrate 10 in which the modified region 11 is formed (for example, FIG. 1) so as to remove at least some of the modified region 11, thereby providing a valley 15 on the surface of the substrate 10 and forming a periodic structure 16 including a plurality of groove portions 12a along one direction which have a surface profile based on the periodic pattern 14 on at least the bottom surface of the valley 15.

When an etching treatment is carried out on the surface of the substrate 10 in which the modified region 11 is formed, the first modified regions 11a are etched more preferentially (selectively) than the second modified regions 11b, thereby forming the valley 15.

At this time, some of the second modified regions 11b remain on the bottom surface of the valley 15 so that a plurality of fins 12b is formed.

The reason why the first modified regions 11a are preferentially etched is that the etching resistance of the first modified regions 11a is low.

For example, in a case in which the substrate 10 is made of silica, the first modified regions 11a lack oxygen so as to become areas having a degraded etching resistance.

The surface profile (the shape of recesses and protrusions) of the periodic structure 16 obtained through alternate formation of the groove portions 12a and the fins 12b is formed based on the periodic pattern 14 in the modified region 11.

That is, the gap between the centers of the adjacent groove portions 12a in the periodic structure 16 corresponds to the gap between the centers of the adjacent modified regions 11a in the periodic pattern 14.

Similarly, the gap between the centers of the adjacent fins 12b in the periodic structure 16 corresponds to the gap between the centers of the adjacent modified regions 11b in the periodic pattern 14.

Therefore, in a case in which the periodic pattern 14 is formed on the order of nanometers, it is possible to similarly form the periodic structure 16 on the order of nanometers.

The plurality of groove portions 12a and fins 12b in the periodic structure 16 are formed along one direction.

The direction is the same direction as the direction in which the first modified regions 11a and the second modified regions 11b stretch in the periodic pattern 14.

Figure 5:
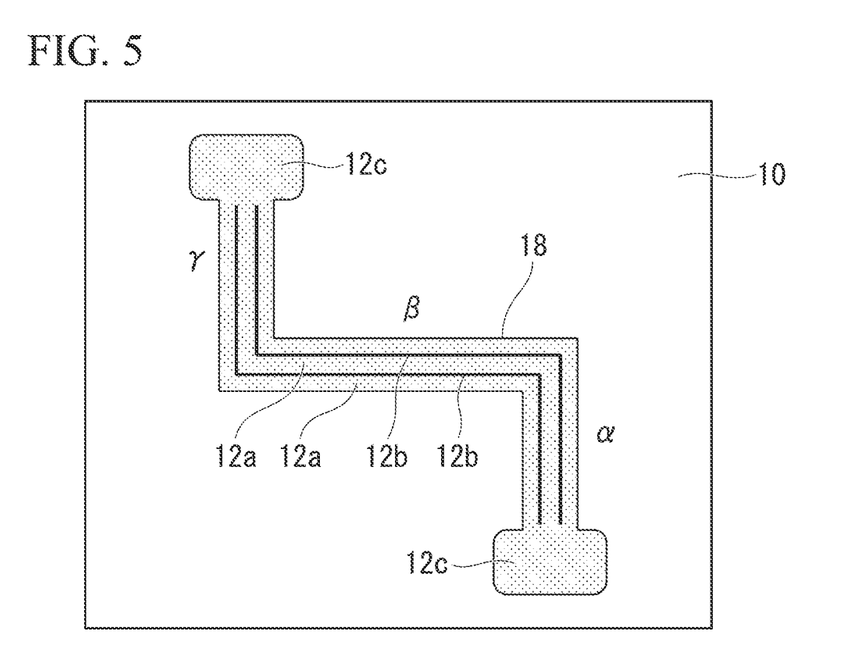
FIG. 5 is an example of a schematic top view of the substrate showing the relationship between the stretching direction of the valley that forms a flow channel and the stretching direction of groove portions and fins in the periodic structure formed on the bottom surface of the valley.
Figure 6:
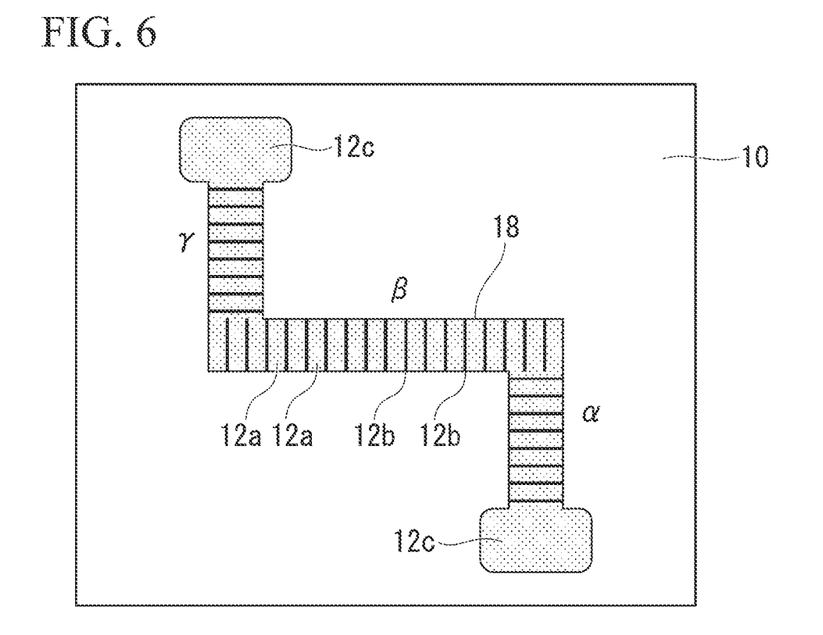
FIG. 6 is another example of the schematic top view of the substrate showing the relationship between the stretching direction of the valley that forms a flow channel and the stretching direction of groove portions and fins in the periodic structure formed on the bottom surface of the valley.

The above fact is shown in FIGS. 5 and 6.

FIG. 5 shows a substrate obtained through an etching treatment of the substrate 10 shown in FIG. 2, in which the groove portions 12a and the fins 12b stretch in a direction along the stretching direction of a flow channel 18 formed after the etching treatment.

In contrast, FIG. 6 shows a substrate obtained through an etching treatment of the substrate 10 shown in FIG. 3, in which the groove portions 12a and the fins 12b stretch in the vertical direction to the stretching direction of the flow channel 18 formed after the etching treatment.

The etching resistance changes depending on the combination of the material of the substrate 10 and the etchant or etching gas.

Therefore, there may be cases in which the second modified regions 11b are more selectively etched so as to form the valley depending on the combination of both.

Even in this case, since the periodic structure 16 based on the periodic pattern 14 is formed, there may be cases in which the microfluidic chip functions as the microfluidic chip according to the invention.

The etching method may be any method of wet etching and dry etching, but is preferentially dry etching in which the shape of the periodic structure 16 can be dynamically controlled, and highly accurate working is possible as described below.

In wet etching, there are cases in which the dynamic shape control is difficult, and a desired periodic structure cannot be obtained.

The dry etching method may be any method of an anisotropic dry etching method and an isotropic dry etching method, but is preferentially the isotropic dry etching from the viewpoint of formation of the valley 15 on the surface of the substrate 10.

When the isotropic dry etching method is used, it is possible to preferentially remove the first modified regions 11a so as to form the groove portions 12a.

Furthermore, it is also possible to carry out etching of the second modified regions 11b to a certain extent so as to form the fins 12b and form valleys 15 on the surface of the substrate 10.

Figure 7:
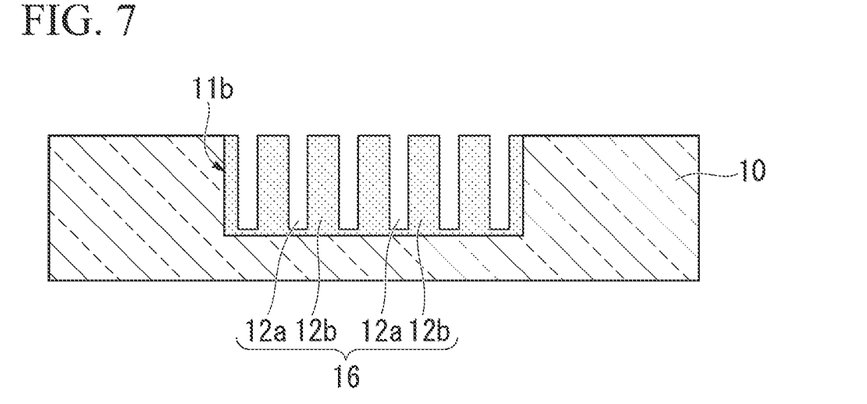
FIG. 7 is a schematic cross-sectional view of the substrate showing a case in which the valley is not formed on the surface of the substrate.

On the other hand, when the anisotropic dry etching method is used, it is possible to selectively remove the first modified regions 11a so as to form the groove portions 12a, but there are cases in which the second modified regions 11b are rarely etched, and the valleys 15 are not formed on the surface of the substrate 10 (refer to FIG. 7).

Based on the above characteristics, the anisotropic etching method and the isotropic etching method may be appropriately combined and used.

For example, in a case in which the groove portions 12a are deeply dug, it is effective to use the anisotropic etching method.

Examples of the anisotropic dry etching method include reactive ion etching (hereinafter referred to as RIE).

More specifically, parallel plate-type RIE, magnetron-type RIE, ICP-type RIE, NLD-type RIE, and the like can be applied.

In addition, it is also possible to apply etching in which neutral particle beams are used.

Examples of the etching gas include fluorocarbon-based gas, SF-based gas, CHF3, fluorine gas, chlorine gas, and the like.

It is possible to appropriately mix other gases, for example, oxygen, argon, or helium, and use the mixture.

In a case in which the anisotropic dry etching method is used, it is possible to control the structure of the valley 15 by changing the process pressure (the pressure in the etching chamber) during etching.

The RF power during etching and the pressure in the chamber are parameters that determine the working shape; however, particularly, a change in the etching pressure is a parameter that most easily controls the shape of the etched periodic structure 16 (surface profile).

In a case in which the pressure is low, since ions are strongly drawn into the material, the material becomes more anisotropic, and it is possible to selectively etch only areas having a high etching selectivity in the periodic structure 16 (the valleys 12a).

Therefore, the modified regions 11b located between the modified regions 11a that form the periodic structure 16 and the material in areas near the modified regions 11b are rarely etched, and the modified regions 11a are selectively etched.

In this case, as shown in FIG. 7, the valley 15 is rarely formed, and the groove portions 12a are selectively formed.

In a case in which the pressure is high, since ions are weakly drawn into the material, and the material is etched in a more isotropic manner, the periodic structure 16 is formed, and the modified regions 11a which are areas having a high etching selectivity are also etched in a transverse direction.

That is, the material in areas near the modified regions 11a (the modified regions 11b) as well as the modified regions 11a are also etched.

Thereby, the valley 15 is formed on the surface of the substrate 10 as shown in FIG. 4.

Furthermore, the periodic structure 16 constituted by the plurality of groove portions 12a and the plurality of fins 12b is formed on the bottom surface of the valley 15.

In addition, during the anisotropic dry etching and isotropic dry etching, the plasma density is preferably decreased as much as possible by decreasing the RF power or the like in order to increase the aspect ratio between the groove portions 12a and the fins 12b.

Conversely, when the plasma density is increased by increasing the RF power or the like, there is a tendency of the aspect ratio between the groove portions 12a and the fins 12b to decrease.

When the isotropic dry etching method is used as the dry etching method, in a case in which the isotropy is strong, it is highly likely that layers having a weak etching resistance (the first modified regions 11a) are more etched so as to form the groove portions 12a, and, at the same time, the groove portions 12a are etched in the transverse direction.

Therefore, it is possible to gradually connect the adjacent valleys 12a and fins 12b from the top portion.

Thereby, as shown in FIG. 4, the valley 15 is formed on the surface of the substrate 10.

Furthermore, the periodic structure 16 constituted by the plurality of groove portions 12a and the plurality of fins 12b is formed on the bottom surface of the valley 15.

Examples of the isotropic etching method include barrel-type plasma etching, parallel plate-type plasma etching, downflow-type chemical dry etching, and the like.

The shapes of the groove portions 12a and the fins 12b which form the periodic structure 16 that is formed at least on the bottom surface of the valley 15 formed through the above processes A and B can be formed into desired size, height, width, and length using the laser radiation intensity in the process A and the etching method in the process B.

For example, the microfluidic chip according to the invention can be used as the micro plate described in Japanese Unexamined Patent Application, First Publication No. 2008-286778 by forming the shape of the periodic structure 16 into the shape described in Japanese Unexamined Patent Application, First Publication No. 2008-286778.

In this case, the cross-sectional shapes of the groove portions 12a and the fins 12b in the periodic structure 16 are rectangular, saw-tooth-like, or sinusoidal, and the gap between the adjacent groove portions 12a is the wavelength or less of measurement laser light, which is, for example, 10 to 800 nm, and the depth of the groove portion 12a (the height of the fin 12b) may be 4 to 400 nm.

When the periodic structure 16 satisfies the above requirements, it is possible to generate surface plasmon resonant light in areas near the periodic structure 16 and detect molecular interactions in the area by irradiation of the measurement laser light from the outside.

In addition, the shape of the valley 15 formed through the above processes A and B can be freely formed into the desired depth, width, and length by adjusting the range scanned by the light-collecting area of the laser light L in the process A.

Figure 9:
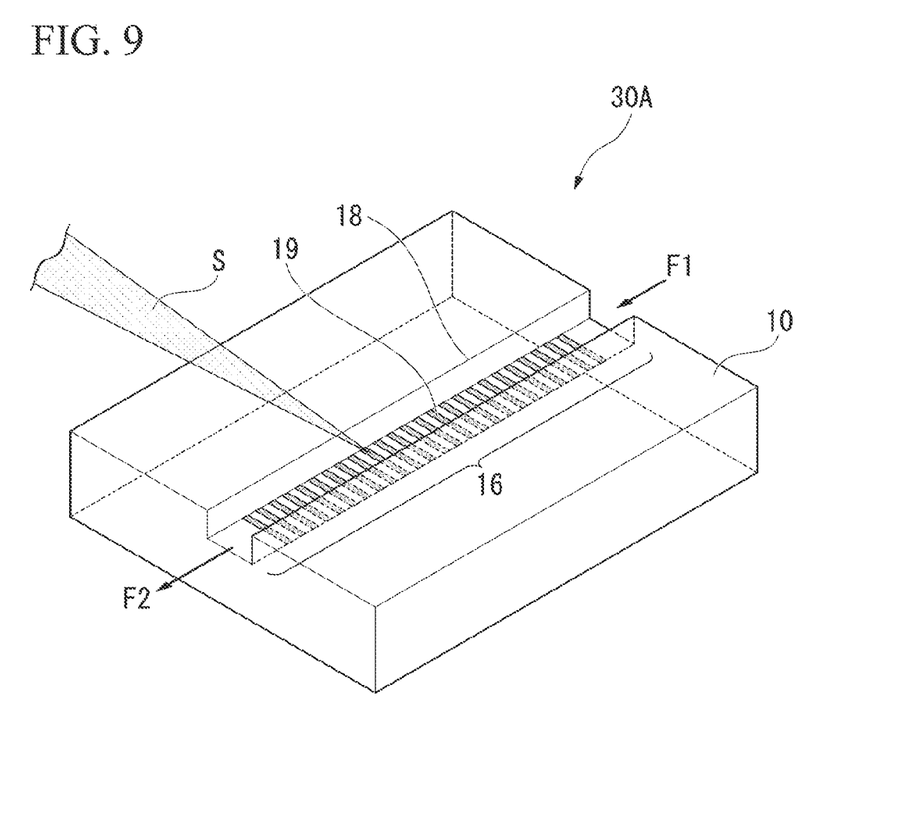
FIG. 9 is a schematic perspective view showing a microfluidic chip according to a first embodiment of the invention.

For example, the valley 15 may be provided so as to form a crank-shaped flow channel 18 as shown in FIGS. 2 and 3, and may be provided so as to form a straight flow channel 18 as shown in FIG. 9.

Figure 11:
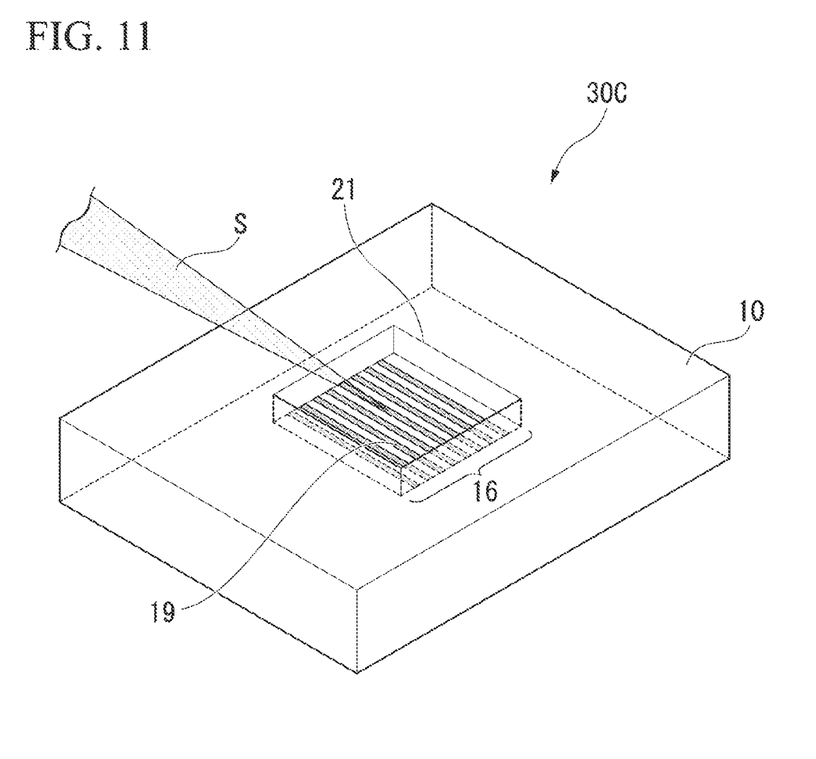
FIG. 11 is a schematic perspective view showing a microfluidic chip according to a second embodiment of the invention.

In addition, the valley 15 may be provided so as to form a rectangular well 21 as shown in FIG. 11.

[Process C]

Figure 8:
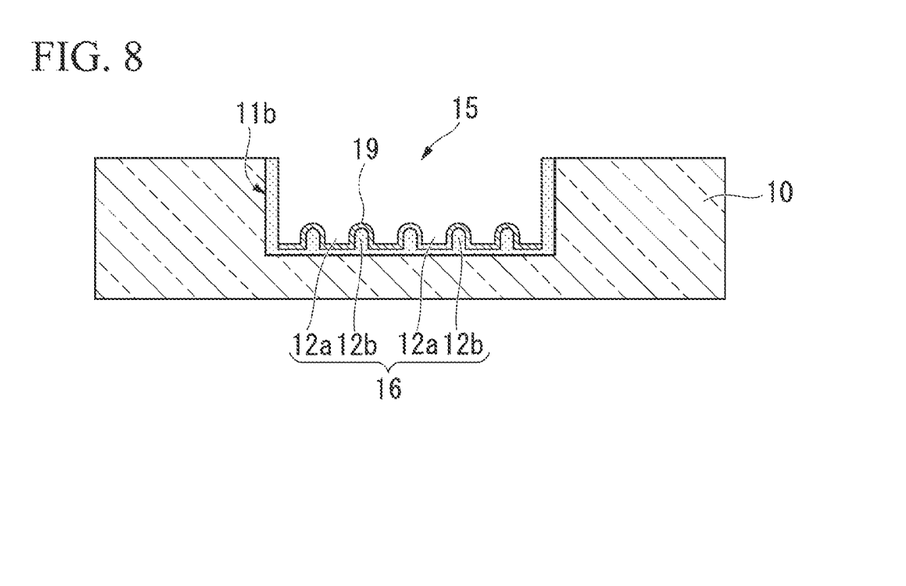
FIG. 8 is a schematic cross-sectional view of the substrate showing a case in which a metal layer is formed so as to cover the periodic structure.

As shown in FIG. 8, the process C is a process in which a metal layer 19 that covers the periodic structure 16 of the bottom surface of the valley 15 is formed.

The material of the metal layer 19 is preferably metal that can generate surface plasmon resonant light when light is radiated from the outside.

Preferable examples thereof include transition metals such as gold, silver, copper, platinum, and nickel.

The thickness of the metal layer 19 is preferably 10 to 500 nm.

The method of forming the metal layer 19 is not particularly limited, and examples thereof that can be employed include well-known thin film-forming method such as a vapor deposition method, a sputtering method, a CVD method, a plating method.

The surface profile of the metal layer 19 (the surface pattern of the metal layer 19) preferably reflects the surface profile of the periodic structure 16.

The surface profile may be substantially the same as the surface profile of the periodic structure 16, or may be a shape in which the metal layer is somewhat smoothed so as to infill the angular portions of the periodic structure 16.

Specifically, for example, the shape of the metal layer described in Japanese Unexamined. Patent Application, First Publication No. 2008-286778 can be referenced.

The method of manufacturing the microfluidic chip of the embodiment may include processes other than the processes A to C described above.

In a case in which a liquid including a measurement specimen is made to flow through the valley 15 formed in the metal layer 19, there are cases in which the metal layer 19 is chemically corroded due to the fluid.

In addition, as described in Japanese Unexamined Patent Application, First Publication No. 2008-286778, there are cases in which fluorescent signals from a measurement subject which is supposed to be detected are quenched due to the metal layer 19.

In order to prevent the above cases, a protective layer (not shown) may be further formed on the metal layer 19.

That is, the manufacturing method according to the embodiment preferably further includes a process in which the protective layer is formed on the metal layer 19.

The material of the protective layer is not particularly limited as long as the material does not absorb much of the external light for generating surface plasmon (measurement laser light) or the fluorescent signals.

Examples thereof include organic polymers such as polycarbonate and polymethacrylate methyl, silica ($SiO_2$), and the like.

The thickness of the protective layer may be determined in accordance with the wavelengths (energies) of the surface plasmon resonant light to be generated and the fluorescent signals, and is generally in a range of 10 to 100 nm.

In addition, as necessary, an adhesive layer may be further provided between the surface of the periodic structure 16 and the metal layer 19 and between the metal layer 19 and the protective layer.

Thereby, the adhesiveness of the each layer can be increased.

Examples of the material of the adhesive layer include chromium, aluminum, titanium, palladium, and the like.

The thickness of the adhesive layer is preferably approximately 0.1 to 3 nm.

The method of forming the protective layer and the adhesive layer is not particularly limited, and a well-known thin film-forming method can be applied.

<Microfluidic Chip>

FIG. 9 shows the microfluidic chip according to the first embodiment.

A microfluidic chip 30A of the first embodiment is a microfluidic chip obtained using the manufacturing method according to the embodiment described above.

The microfluidic chip 30A has the flow channel 18 formed on the surface of the substrate 10.

The periodic structure 16 covered with the metal layer 19 is formed on the bottom surface of the flow channel 18.

It is possible to generate surface plasmon resonant light in areas near the bottom surface of the flow channel 18 by irradiation of the measurement laser light S toward the periodic structure 16.

The measurement laser light S is preferably p-polarized light.

The p polarization preferably includes components in the direction of the periodic structure 16 (the stretching direction of the flow channel 18).

It is possible to observe the state of an observation subject in a measurement specimen solution by making the measurement specimen solution (not shown) flow from one end side (a first end side) F1 to the other end side (a second end side) F2 of the flow channel 18, and, furthermore, by irradiation of the measurement laser light S so as to generate surface plasmon resonant light.

Regarding a specific measurement method, for example, the method described in Japanese Unexamined Patent Application, First Publication No. 2008-286778 can be referenced.

Figure 10:
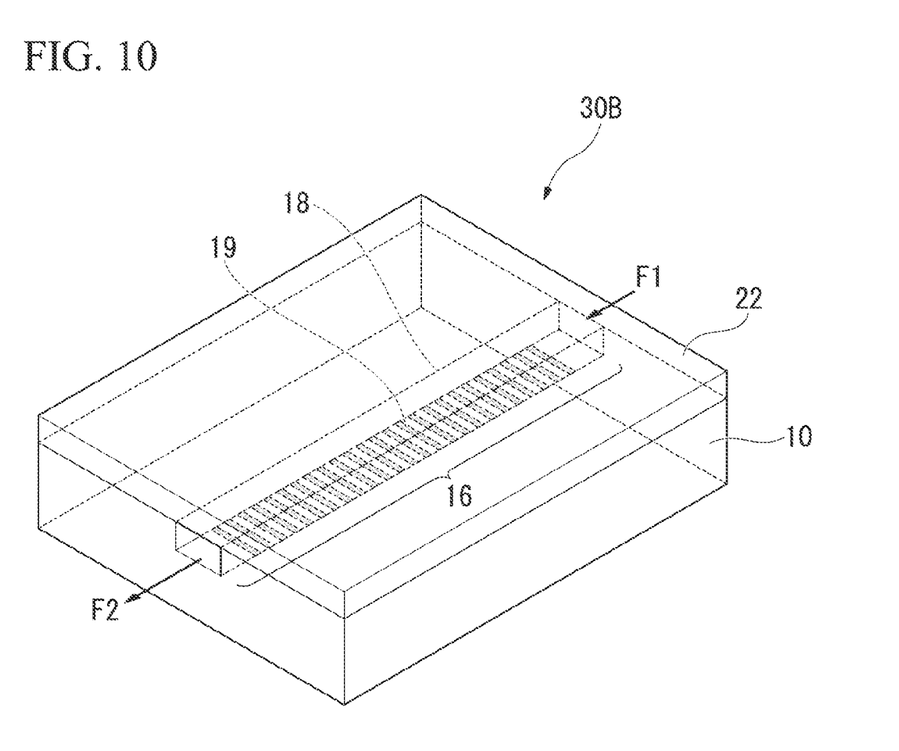
FIG. 10 is a schematic perspective view showing a modified example of the microfluidic chip according to the same embodiment.

In addition, as a modified example of the first embodiment, a configuration in which a member 22 is attached to the surface of the substrate 10 so as to cover the flow channel 18 may be employed as a microfluidic chip 30B shown in FIG. 10.

Covering the flow channel 18 can prevent the specimen solution made to flow in the flow channel 18 from overflowing outside the flow channel 18.

Furthermore, it also becomes possible to apply a pressure to the specimen solution and make the solution flow in the flow channel 18.

Therefore, the manufacturing method according to the above embodiment preferably further includes a process in which the member 22 is attached to the surface of the substrate 10 so as to cover the flow channel 18 on the surface of the substrate 10.

The material of the member 22 is not particularly limited as long as the material does not absorb much of the measurement laser light S or the fluorescent signals, and examples thereof include silica glass substrates.

The method of attaching the substrate 10 and the member 22 is not particularly limited, and a well-known method may be carried out.

FIG. 11 shows a microfluidic chip according to the second embodiment of the invention.

A microfluidic chip 30C of the second embodiment is a microfluidic chip obtained using the manufacturing method according to the embodiment described above.

The microfluidic chip 30C has the well 21 formed on the surface of the substrate 10.

The periodic structure 16 covered with the metal layer 19 is formed on the bottom surface of the well 21.

It is possible to generate surface plasmon resonant light in areas near the bottom surface of the well 21 by irradiation of the measurement laser light S toward the periodic structure 16.

Therefore, it is possible to observe the state of an observation subject in a measurement specimen solution (not shown) by storing (flowing in) the measurement specimen solution in the well 21, and, furthermore, by irradiation of the measurement laser light S so as to generate surface plasmon resonant light.

Regarding a specific measurement method, for example, the method described in Japanese Unexamined Patent Application, First Publication No. 2008-286778 can be referenced.

<Apparatus for Generating Surface Plasmon Resonant Light>

The apparatus for generating surface plasmon resonant light according to the embodiment is an apparatus for generating surface plasmon resonant light in which the microfluidic chip according to the embodiment described above is used.

A periodic structure covered with the above metal layer is formed on the bottom surface of a valley provided on the surface of the substrate of the microfluidic chip.

It is possible to generate surface plasmon resonant light in areas near the periodic structure by irradiating, with light, the periodic structure from the outside.

The valley has a shape that can store a liquid on the surface of the substrate.

Therefore, it is possible to radiate the surface plasmon resonant light to the specimen solution by storing a specimen solution in the valley.

Therefore, it is possible to observe the influences of the surface plasmon resonant light on a measurement subject in the specimen solution by separately providing an observing apparatus such as a microscope.

The method of manufacturing a microfluidic chip, microfluidic chip, and apparatus for generating surface plasmon resonant light of the invention can be widely used for using and manufacturing such as molecular interaction detecting apparatuses in which a surface plasmon resonant light is used, surface plasmon excitation fluorescent-enhanced fluorescent microscopes, and fluorescent micro plate readers.

What is claimed is:

1. A method of manufacturing a microfluidic chip, comprising:
   irradiating, with a laser light, an area to be provided with a valley for storing a fluid on a surface of a substrate so as to form a modified region having a periodic pattern formed in a self-organizing manner in a light-collecting area of the laser light, the laser light having a pulse width for which the pulse duration is on the order of picoseconds or less;
   carrying out an etching treatment on the substrate in which the modified region is formed, removing at least some of the modified portion so as to provide the valley, and forming a periodic structure having a plurality of groove portions along one direction which have a surface profile based on the periodic pattern on at least a bottom surface of the valley; and
   forming a metal layer that covers the periodic structure of the bottom surface, wherein
   the irradiating step further comprises: using linear polarized laser as the laser light; and scanning the light-collecting area of the laser light while controlling the polarized wave direction of the linear polarized laser so that an angle between the scanning direction of the laser light and the polarized wave direction is constant.

2. The method of manufacturing a microfluidic chip according to claim 1,
   wherein the periodic pattern formed in a self-organizing manner comprises:
   portions modified by the constructive interference of interference waves of a plasmon in an area near the surface of the substrate which is generated by the laser light incident to the substrate and the incident laser light; and
   portions modified by the destructive interference of the interference waves.

3. The method of manufacturing a microfluidic chip according to claim 1, wherein
   the irradiating step further comprises scanning the light-collecting area of the laser light in a vertical direction to a polarized wave direction of the straight polarized light so that the scanning direction and a direction in which the plurality of groove portions which form the periodic structure is stretched are parallelized.

4. The method of manufacturing a microfluidic chip according to claim 1, wherein
   the irradiating step further comprises scanning the light-collecting area of the laser light in a parallel direction to a polarized wave direction of the straight polarized light so that a direction in which the plurality of groove portions which form the periodic structure is stretched are made to be vertical to the scanning direction.

5. The method of manufacturing a microfluidic chip according to claim 1, wherein an isotropic dry etching method is used in the etching treatment.

6. The method of manufacturing a microfluidic chip according to claim 1, wherein the valley provided on the surface of the substrate forms a flow channel.

7. The method of manufacturing a microfluidic chip according to claim 6, the method further comprising:

attaching a member to the surface of the substrate so as to cover the flow channel on the surface of the substrate.

8. The method of manufacturing a microfluidic chip according to claim 1, wherein the valley provided on the surface of the substrate forms a well.

9. The method of manufacturing a microfluidic chip according to claim 1, the method further comprising: forming a protective layer on the metal layer.

10. A microfluidic chip obtained using the manufacturing method according to claim 1.

11. An apparatus for generating surface plasmon resonant light, wherein the microfluidic chip according to claim 10 is used.

* * * * *